United States Patent
Sternby

(10) Patent No.: US 12,161,791 B2
(45) Date of Patent: *Dec. 10, 2024

(54) MULTIPART FLUID SYSTEM AND A SYSTEM FOR REGIONAL CITRATE ANTICOAGULATION IN AN EXTRACORPOREAL BLOOD CIRCUIT

(71) Applicant: GAMBRO LUNDIA AB, Lund (SE)

(72) Inventor: Jan Sternby, Lund (SE)

(73) Assignee: GAMBRO LUNDIA AB, Lund (SE)

( * ) Notice: Subject to any disclaimer, the term of this patent is extended or adjusted under 35 U.S.C. 154(b) by 1211 days.

This patent is subject to a terminal disclaimer.

(21) Appl. No.: 16/902,545

(22) Filed: Jun. 16, 2020

(65) Prior Publication Data

US 2020/0306441 A1    Oct. 1, 2020

Related U.S. Application Data

(60) Continuation of application No. 15/345,126, filed on Nov. 7, 2016, now Pat. No. 10,709,833, which is a (Continued)

(30) Foreign Application Priority Data

Mar. 31, 2009    (SE) .................................. 0900422-7

(51) Int. Cl.
*A61M 1/36*    (2006.01)
*A61K 31/191*    (2006.01)
(Continued)

(52) U.S. Cl.
CPC ......... *A61M 1/3672* (2013.01); *A61K 31/191* (2013.01); *A61K 31/194* (2013.01); (Continued)

(58) Field of Classification Search
CPC ... A61K 2300/00; A61M 1/16; A61M 1/3672; A61M 1/3431; A61M 1/3434
See application file for complete search history.

(56) References Cited

U.S. PATENT DOCUMENTS

| | | |
|---|---|---|
| 3,941,565 A | 3/1976 | Schwartz |
| 4,000,072 A | 12/1976 | Sato et al. |
| (Continued) | | |

FOREIGN PATENT DOCUMENTS

| | | |
|---|---|---|
| EP | 0437274 A1 | 7/1991 |
| EP | 1430920 A1 | 6/2004 |
| (Continued) | | |

OTHER PUBLICATIONS

International Preliminary Report on Patentability issued in International Application No. PCT/US2010/038985; Date of report: Dec. 20, 2011.

(Continued)

*Primary Examiner* — Leslie R Deak
(74) *Attorney, Agent, or Firm* — K&L Gates LLP

(57) ABSTRACT

A method of treating blood withdrawn from patient including: simultaneously withdrawing blood and infusing withdrawn blood from and to the patient by flowing the withdrawn blood through an extracorporeal dialysis circuit including a dialyzer having a semi-permeable dialysis membrane and a dialysate side adjacent the membrane; feeding a dialysate containing 1 to 5 mM total calcium and 2 to 8 mM citrate to the dialysate side of the dialyzer, and introducing an anticoagulation fluid including at least 8 mM citrate into the withdrawn blood upstream of the dialyzer.

19 Claims, 4 Drawing Sheets

Related U.S. Application Data division of application No. 14/553,417, filed on Nov. 25, 2014, now Pat. No. 9,486,570, which is a division of application No. 13/260,635, filed as application No. PCT/EP2010/054267 on Mar. 31, 2010, now Pat. No. 8,911,390.

(60) Provisional application No. 61/164,922, filed on Mar. 31, 2009.

(51) Int. Cl.

| | | |
|---|---|---|
| *A61K 31/194* | (2006.01) | |
| *A61K 31/7004* | (2006.01) | |
| *A61K 33/06* | (2006.01) | |
| *A61K 33/10* | (2006.01) | |
| *A61K 33/14* | (2006.01) | |
| *A61K 33/20* | (2006.01) | |
| *A61K 33/42* | (2006.01) | |
| *A61M 1/16* | (2006.01) | |

(52) U.S. Cl.
CPC .......... *A61K 31/7004* (2013.01); *A61K 33/06* (2013.01); *A61K 33/10* (2013.01); *A61K 33/14* (2013.01); *A61K 33/20* (2013.01); *A61K 33/42* (2013.01); *A61M 1/16* (2013.01)

(56) References Cited

U.S. PATENT DOCUMENTS

| | | | |
|---|---|---|---|
| 5,252,213 A | 10/1993 | Ahmad et al. | |
| 5,437,864 A | 8/1995 | Edgington et al. | |
| 5,730,713 A | 3/1998 | Okarma et al. | |
| 6,200,287 B1 | 3/2001 | Keller et al. | |
| 6,610,206 B1 | 8/2003 | Callan et al. | |
| 7,351,218 B2* | 4/2008 | Bene | A61M 1/3672 604/6.07 |
| 8,911,390 B2* | 12/2014 | Sternby | A61K 33/42 604/4.01 |
| 2004/0048837 A1 | 3/2004 | Lazarus | |
| 2004/0060865 A1 | 4/2004 | Callan et al. | |
| 2004/0230152 A1 | 11/2004 | Bainbridge et al. | |
| 2005/0236330 A1 | 10/2005 | Nier et al. | |
| 2005/0276868 A1 | 12/2005 | Degreve et al. | |
| 2007/0062861 A1 | 3/2007 | Lannoy | |
| 2007/0066928 A1 | 3/2007 | Lannoy | |
| 2007/0270341 A1 | 11/2007 | Morley et al. | |
| 2008/0015487 A1 | 1/2008 | Szamosfalvi et al. | |
| 2008/0280955 A1 | 11/2008 | McCamish | |
| 2009/0221948 A1 | 9/2009 | Szamosfalvi | |

FOREIGN PATENT DOCUMENTS

| | | |
|---|---|---|
| JP | 2008-502722 | 1/2008 |
| WO | 01/21233 A1 | 3/2001 |
| WO | 2007/101064 A2 | 9/2007 |
| WO | 2008157748 | 12/2008 |
| WO | 2009026603 A1 | 3/2009 |
| WO | 2010029401 A2 | 3/2010 |

OTHER PUBLICATIONS

International Search Report and Written Opinion, PCT/US2010/038985, mailing date Oct. 5, 2010.

Daugirdas, J.T., et al., Handbook of Dialysis, pp. 204-251 (2007).

Bohler, J., et al., "Reduction of Granulocyte Activation During Hemodialysis with Regional Citrate Anticoagulation: Dissociation of Complement Activation and Neutropenia from Neutrophil Degranulation," J. Am. Soc. Nephrol., 7:234-241 (1996).

Gabutti, L., et al., "The Favorable Effect of Regional Citrate Anticoagulation on Interleukin-1 Beta Release is Dissociated from Both Coagulation and Complement Activation," J. Nephrol., 17:819-825 (2004).

Gritters, M., et al., "Citrate Anticoagulation Abolishes Degranulation of Polymorphonuclear Cells and Platelets and Reduces Oxidative Stress During Haemodialysis," Nephrol. Dial. Transplant, 21:153-159 (2006).

Hofbauer, R., et al., "Effect of Anticoagulation on Blood Membrane Interactions During Hemodialysis," Kidney Int., 56:1578-1583 (1999).

Dittrich, et al., J. Am. Soc. Nephrol., 19, pp. 461A, Abstract F-P01576 (2008).

Kozik-Jaromin, J., "Citrate Kinetics During Regional Citrate Anticoagulation in Extracorporeal Organ Replacement Therapy," Internal Medicine, IV, Nephrology (2005).

Runolfur Palsson et al., "Regional Citrate Anticoagulation In Continuous Venovenous Hemofiltration In Critically Ill Patients With A High Risk of Bleeding", Kidney International, vol. 55, (1999), pp. 1991-1997.

Ashita J. Tolwani et al., "Simplified Citrate Anticoagulation For Continuous Renal Replacement Therapy", Kidney International, vol. 60, (2001), pp. 370-374.

Slonim, A., et al. "Pediatric Critical Care Medicine", Lippincott, Williams & Wilkins: Jan. 2006.

* cited by examiner

MULTIPART FLUID SYSTEM AND A SYSTEM FOR REGIONAL CITRATE ANTICOAGULATION IN AN EXTRACORPOREAL BLOOD CIRCUIT

PRIORITY CLAIM

This application is a continuation of U.S. patent application Ser. No. 15/345,126, filed Nov. 7, 2016, which is a divisional of U.S. patent application Ser. No. 14/553,417, filed Nov. 25, 2014 (now U.S. Pat. No. 9,486,570), which is a divisional of Ser. No. 13/260,635, filed Sep. 27, 2011 (now U.S. Pat. No. 8,911,390), which is the U.S. national phase of international application PCT/EP2010/054267, filed Mar. 31, 2010, which claims priority to Swedish Patent Application No. 0900422-7, filed Mar. 31, 2009 and U.S. Provisional Application 61/164,922, filed Mar. 31, 2009. The entire contents of each of the above applications are hereby incorporated by reference and relied upon.

TECHNICAL FIELD

The present invention concerns a multipart fluid system for use in CRRT. More particularly it relates to an anticoagulation fluid and at least one fluid from the group consisting of a dialysis fluid and an infusion fluid.

The present invention further concerns a system for regional anticoagulation in an extracorporeal blood treatment.

BACKGROUND

Dialysis is the indicated treatment for patients with renal insufficiency. The removal of waste substances and excess of fluid from the blood is effected by transfer to an external fluid or by replacement of plasma liquid with an external fluid. Various dialysis techniques with associated dialysis fluids, may be differentiated. Which dialysis technique to use, depend on the type of patient.

In the case of patients suffering from acute renal insufficiency, a continuous treatment throughout the entire day for several weeks, a continuous renal replacement therapy (CRRT), is the indicated treatment.

Continuous renal replacement therapy (CRRT) is also the treatment mode when a patient with chronic renal insufficiency is using a wearable artificial kidney system, such a system is for example disclosed in US 2008/058696.

In a CRRT treatment a portion of the patient's blood stream is lead into an extracorporeal blood circuit comprising a semipermeable membrane in which the removal of waste substances and excess fluid is performed and then the cleansed blood is lead back to the patient. The semipermeable membrane has a blood side and a dialysate side.

When the removal of waste substances and excess fluid is effected by transfer to an external fluid, the waste substances and excess fluid are transferred by diffusion through the semipermeable membrane wall into a dialysis fluid flowing on the dialysate side of the semipermeable membrane. This technique is called hemodialysis.

When the removal of waste substances and excess fluid is made by replacement of plasma liquid with an external fluid, a portion of the plasma liquid is removed from the blood by means of convective flow through the semipermeable membrane, and an external fluid (also called a replacement fluid or an infusion fluid) is added to the blood stream. This technique is called hemofiltration.

Finally the removal of waste substances and excess fluid may also be made by a combination of hemodialysis and hemofiltration, thus the removal of waste substances and excess fluid is provided by a combination of diffusion and convection through the semipermeable membrane. This technique is called hemodiafiltration.

Common for all the above disclosed techniques is that the blood is withdrawn from the patient continuously into an extracorporeal blood circuit, in which the removal takes place, and the "cleansed" blood is returned to the patient. When blood is removed from its normal environment within the blood vessels, the blood coagulation cascade is initiated, and in order not to clog the extracorporeal blood circuit with the coagulating blood, means for anticoagulation have to be provided.

The use of citrate as an anticoagulant for intensive care patients is increasing. A fluid containing sodium citrate and/or citric acid is then infused close to the blood access where the blood exits the patient and enters into the extracorporeal blood circuit. Citrate acts as an anticoagulant by lowering the ionized calcium concentration within the plasma, through calcium citrate complex formation. Ionized calcium is essential for the blood coagulation cascade. If the ionized calcium level is lowered well below 0.5 mM, the blood coagulation cascade is prevented. Citrate that exists in the blood is rapidly metabolized in the liver, forming three bicarbonate ions per citrate ion. As the citrate concentration is lowered in the metabolism, citrate complex bound calcium is released and returns to ionized calcium.

Today the use of citrate as anticoagulant is usually combined with the use of a dialysis fluid or an infusion fluid not containing any calcium, which means that a significant amount of calcium will be removed in the semipermeable membrane. This calcium has to be replaced in order not to create dangerously low levels of ionized calcium in the blood of the patient. The replacement of removed calcium is usually done by direct infusion of a fairly concentrated calcium fluid, either calcium chloride or, in increasing number of cases, calcium gluconate. This infusion may be done either into the line set for the extracorporeal blood circuit, close to the blood return to the patient, or directly into the vein of the patient.

The balancing of the correct amount of calcium within the blood in order to replace the removal in the semipermeable membrane is a delicate matter. Both too much and too little calcium within the blood may lead to serious patient injury, and if not handled correctly it is potentially fatal to the patient. A close supervision of the patient's ionized calcium level is therefore necessary. Many attempts have therefore been made to avoid the calcium infusion by having calcium in the dialysis and/or infusion fluids. However, it is difficult to have enough calcium in these fluids without causing clotting problems.

SUMMARY OF THE INVENTION

One object of the present invention is to provide a multipart fluid system for citrate anticoagulation with which the removal of calcium within the dialysis process is reduced or prevented without increasing the risk of clotting.

The present invention concerns a multipart fluid system for use in CRRT, wherein the multipart fluid system comprises an anticoagulation fluid and at least one fluid from the group consisting of a dialysis fluid and an infusion fluid. According to the invention the anticoagulation fluid comprises at least 8 mM citrate, and the dialysis fluid and/or infusion fluid comprises 2-8 mM citrate and 1-5 mM total calcium.

In one embodiment of the present invention said anticoagulation fluid further comprises 1.5-4 mM total calcium. In another embodiment said anticoagulation fluid comprises 2-3 mM total calcium. In a further embodiment said anticoagulation fluid comprises 2.2-2.6 mM total calcium. In another embodiment said anticoagulation fluid comprises about 2.4 mM total calcium.

In another embodiment of the present invention said anticoagulation fluid comprises 8-50 mM citrate. In a further embodiment said anticoagulation fluid comprises 10-50 mM citrate. In even a further embodiment said anticoagulation fluid comprises 17-50 mM citrate. In a further embodiment said anticoagulation fluid comprises 18-50 mM citrate.

In even another embodiment of the present invention said anticoagulation fluid further comprises 0-1.5 mM magnesium, 0-5.0 mM potassium, 0-11 mM glucose, 130-150 mM sodium and 0-140 mM chloride.

In one embodiment of the present invention the dialysis fluid and/or infusion fluid comprises 2.0-7.0 mM citrate and 1.8-2.4 mM total calcium. In another embodiment the dialysis fluid and/or infusion fluid comprises 3.0-5.0 mM citrate and 1.8-2.4 mM total calcium.

In even another embodiment of the present invention, the dialysis and/or infusion fluid further comprises 0-1.5 mM magnesium, 0-5.0 mM potassium, 0-11 mM glucose, 130-150 mM sodium and 80-150 mM chloride, and 0-2.8 mM phosphate.

In another embodiment of the present invention, the dialysis and/or infusion fluid further comprises a physiological buffer. In one embodiment said physiological buffer is bicarbonate. In another embodiment the dialysis fluid and/or infusion fluid comprises <25 mM bicarbonate.

In yet another embodiment said dialysis and/or infusion fluid further comprises 0.1-3.0 mM gluconic acid.

In another embodiment said dialysis and/or infusion fluid further comprises 0.5-2.9 mM gluconic acid.

In even a further embodiment said infusion fluid is to be used as post infusion fluid.

In another embodiment said multipart fluid system only comprises an anticoagulation fluid and a dialysis fluid according to above embodiments.

In another embodiment said multipart fluid system only comprises an anticoagulation fluid and at least one infusion fluid according to above embodiments.

In another embodiment said multipart fluid system only comprises an anticoagulation fluid, a dialysis fluid and at least one infusion fluid according to above embodiments.

In another embodiment said multipart fluid system does not comprise a post infusion fluid comprising >6 mM total calcium.

The present invention further concerns a system for regional citrate anticoagulation in an extracorporeal blood circuit comprising an arterial blood line configured to be connected to a vascular access for withdrawing blood from a patient and a venous blood line configured to be connected to the vascular access for returning blood to the patient. According to the present invention this system comprises a filter (a semipermeable membrane) with a dialysate side and a blood side, which blood side is in fluid communication with the arterial and venous blood lines; a pre-filter infusion line connected to the arterial blood line upstream the filter and connected to an anticoagulation fluid source containing at least 8 mM citrate to be infused into the blood stream in the arterial blood line; and a post-filter infusion line connected to the venous blood line downstream the filter and connected to an infusion fluid source comprising 2-8 mM citrate and 1-5 mM total calcium to be infused into the blood stream in the venous blood line. Thus, the pre-filter infusion line is in fluid communication with an anticoagulation fluid source containing at least 8 mM citrate, and the post-filter infusion line is in fluid communication with an infusion fluid source comprising 2-8 mM citrate and 1-5 mM total calcium.

In another embodiment of this system the dialysate side of the filter is in fluid communication with a dialysis fluid source comprising 2-8 mM citrate and 1-5 mM total calcium.

In even another embodiment of this system, this system does not comprise any post-filter infusion line being in fluid communication with any infusion fluid sources comprising >6 mM total calcium. A post-filter infusion line being an infusion line connected to the venous blood line downstream the filter. Thus, no post-filter infusion line is connected to an infusion fluid source comprising >6 mM total calcium.

The present invention further concerns a system for regional citrate anticoagulation in an extracorporeal blood circuit comprising an arterial blood line configured to be connected to a vascular access for withdrawing blood from a patient and a venous blood line configured to be connected to the vascular access for returning blood to the patient. According to the present invention this system comprises a filter with a dialysate side and a blood side, which blood side is in fluid communication with the arterial and venous blood lines, and which dialysate side is in fluid communication with a dialysis fluid source comprising 2-8 mM citrate and 1-5 mM total calcium; and a pre-filter infusion line connected to the arterial blood line upstream the filter and connected to an anticoagulation fluid source containing at least 8 mM citrate to be infused into the blood stream in the arterial blood line.

In another embodiment of this system, this system does not comprise any post-filter infusion line being connected to any infusion fluid sources comprising >6 mM total calcium. Thus, the pre-filter infusion line is in fluid communication with an anticoagulation fluid source containing at least 8 mM citrate, and no post-filter infusion line is connected to any infusion fluid sources comprising >6 mM total calcium.

The present invention further concerns a system for regional citrate anticoagulation in an extracorporeal blood circuit comprising an arterial blood line configured to be connected to a vascular access for withdrawing blood from a patient and a venous blood line configured to be connected to the vascular access for returning blood to the patient. According to the present invention this system comprises a filter with a dialysate side and a blood side, which blood side is in fluid communication with the arterial and venous blood lines; a first pre-filter infusion line connected to the arterial blood line upstream the filter and connected to an anticoagulation fluid source containing at least 8 mM citrate to be infused into the blood stream in the arterial blood line; and a second pre-filter infusion line connected to the arterial blood line upstream the filter and connected to an infusion fluid source comprising 2-8 mM citrate and 1-5 mM total calcium to be infused into the blood stream in the arterial blood line. Thus, the first pre-filter infusion line is in fluid communication with an anticoagulation fluid containing at least 8 mM citrate, and the second pre-filter infusion line is in fluid communication with an infusion fluid source comprising 2-8 mM citrate and 1-5 mM total calcium.

In another embodiment this system further comprises a post-filter infusion line connected to the venous blood line downstream the filter and connected to an infusion fluid source comprising 2-8 mM citrate and 1-5 mM total calcium to be infused into the blood stream in the venous blood line. Thus, the post-infusion line is in fluid communication with an infusion fluid source comprising 2-8 mM citrate and 1-5 mM total calcium.

In yet another embodiment of this system the dialysate side of the filter is in fluid communication with a dialysis fluid comprising 2-8 mM citrate and 1-5 mM total calcium.

In even another embodiment of this system, this system does not comprise any post-filter infusion line being connected to any infusion fluid sources comprising >6 mM total calcium.

In other embodiments of the systems according to the present invention, said anticoagulation fluid further comprises 1.5-4 mM total calcium.

Yet another embodiment of the systems according to the present invention further comprises a control unit configured to control the anticoagulation fluid flow rate in relation to the blood flow rate. By having such a control unit, the system is monitoring and securing that the amount of citrate within the blood is enough to avoid coagulation within the extracorporeal blood circuit.

With the multipart fluid systems according to the present invention and the systems for regional citrate anticoagulation in an extracorporeal blood circuit according to the present invention it has surprisingly been shown that a separate calcium infusion may be avoided.

DEFINITIONS

Figure 1:
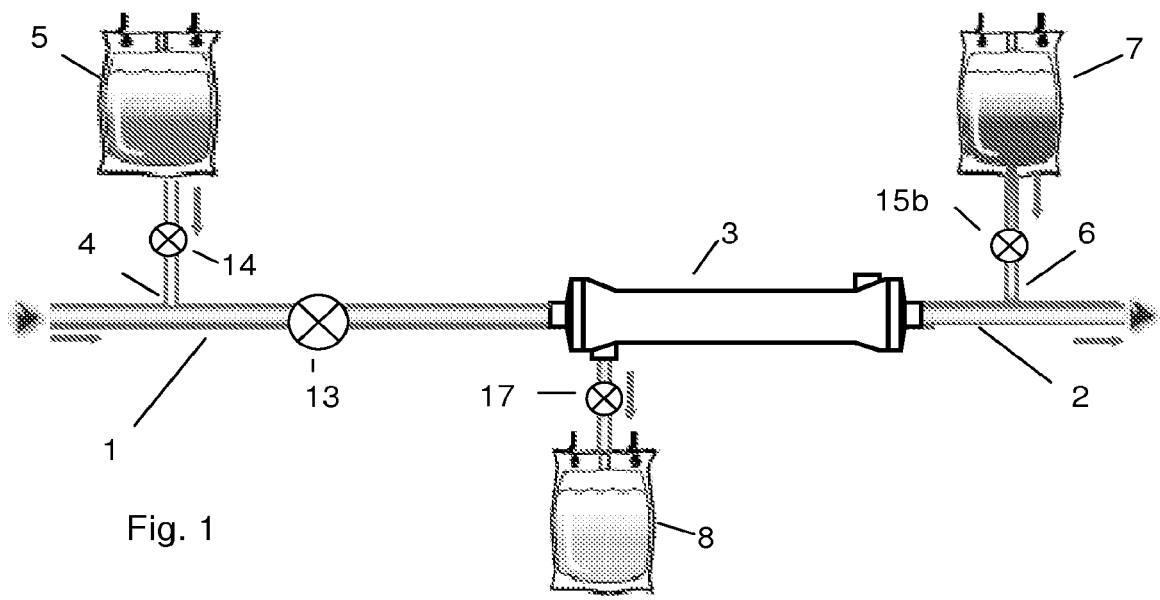
FIGS. 1 to 8 show different embodiments of the system for regional citrate anticoagulation in an extracorporeal blood circuit.

The term "CRRT" means a continuous renal replacement therapy and this type of treatment mode is used in case of acute renal insufficiency or in case of chronic renal insufficiency when using a wearable artificial kidney system.

The term "anticoagulation fluid" means a fluid which is intended to provide for the anticoagulation effect within the extracorporeal blood circuit and which is intended to be infused within the extracorporeal blood circuit.

The term "dialysis fluid" means a fluid for perfusion of a filter (also called a semipermeable membrane, a dialyzer, a dialysis filter or a dialysis membrane) on the dialysate side of such a filter.

The term "infusion fluid" means a fluid which is infused into the extracorporeal blood circuit either for predilution, i.e. infused into the extracorporeal blood flow before the blood enters the dialyzer, or for postdilution, i.e. infused into the extracorporeal blood flow after the blood has exited the dialyzer and before the blood is returned to the patient. Infusion fluids is normally also named as replacement fluids, substitution fluids or hemofiltration fluids.

The term "total calcium concentration" means the total amount of calcium present in a fluid, thus representing the sum of calcium present as ionized, complex bound and protein bound calcium.

The term "gluconic acid" means that the component may be added as gluconic acid, glucono-δ-lactone or as its sodium, calcium, magnesium or potassium salt thereof, i.e. gluconate, to the ready-for-use dialysis solution.

The term "citric acid" means that the component may be added as citric acid or as its sodium, magnesium or potassium salt thereof, i.e. citrate, to the ready-for-use dialysis solution.

DETAILED DESCRIPTION OF THE INVENTION

New treatment modalities have been suggested and have been evaluated by use of an in-house software application CitRRT (Rada 20051). The program computes equilibrium concentrations of species present in plasma and fluids used for dialysis by use of equilibrium constants (SCD base 20012). The species (electrolytes, albumin and formed complexes) taken into account are shown in Table 1.

TABLE 1

Normal plasma concentration of electrolytes and albumin together with the complexes taken into account formed with Ca2+ and Mg2+.

| Specie | Normal plasma total cone (mM) (Kratz 1998[3]) | Complex formation with $Ca^{2+}$ and $Mg^{2+}$ |
|---|---|---|
| $Ca^{2+}$ | 2.1-2.6 (1.1-1.3 ionized) | |
| $Mg^{2+}$ | 0.7-1.0 | |
| $Na^+$ | 135-145 | |
| $Cl^-$ | 100-108 | |
| $HCO_3^-$, bicarbonate, bic | 22-26 | $CaHCO_3^+$, $MgHCO_3^+$ |
| $C_6H_5O_7^{3-}$, citrate, cit | 0.1-0.3 (infants, Ames19504) | Ca-cit$^-$, Ca-cit$_2^{4-}$, Mg-cit$^-$. Mg-cit$_2^{4-}$ |
| Albumin, alb | 0.5-0.6 | Alb-Ca$_n$, alb-Mg$_n$, n = 1-10 |

The requirements of the treatments are:
1. An adequate dialysis treatment
2. A sufficient anticoagulant effect, i.e. the ionized calcium through the blood side of the filter (dialyzer) must be 0.2-0.5 mM, preferably 0.3-0.4 (according to literature)
3. The total plasma concentration of calcium when returned to the patient has to be at normal level, i.e. about 2.5 mM. Other electrolyte concentration levels must also be satisfactory.

Four different treatment modalities were evaluated, also shown in Table 2, and these are:
1. As common today, with citrate and NaCl in the anticoagulation fluid, all normal ions except $Ca^{2+}$ in the dialysis fluid, and infusion of $Ca^{2+}$ from a calcium syringe.
2. Citrate and NaCl in the anticoagulation fluid, all normal ions including $Ca^{2+}$ in the dialysis fluid. To investigate if additional $Ca^{2+}$ from a calcium syringe may be avoided.
3. Citrate and NaCl in the anticoagulation fluid, citrate plus all normal ions including $Ca^{2+}$ in the dialysis fluid. To investigate if additional $Ca^{2+}$ from a calcium syringe may be avoided.

4. Citrate plus all normal ions including $Ca^{2+}$ in the anticoagulation fluid, citrate plus all normal ions in the dialysis fluid. To investigate if additional $Ca^{2+}$ from a calcium syringe may be avoided.

TABLE 2

The evaluated treatment modalities:

| Modality | Anticoagulation fluid | Dialysis fluid | Calcium infusion mandatory? |
|---|---|---|---|
| 1. | $Cit^{3-}$, $Na^+$, $Cl^-$ | $Na^+$, $Mg^{2+}$, $K^+$, $HCO_3^-$, $Cl^-$ | Yes |
| 2. | $Cit^{3-}$, $Na^+$, $Cl^-$ | $Ca^{2+}$, $Na^+$, $Mg^{2+}$, $K^+$, $HCO_3^-$, $Cl^-$ | ? |
| 3. | $Cit^{3-}$, $Na^+$, $Cl^-$ | $Cit^{3-}$, $Ca^{2+}$, $Na^+$, $Mg^{2+}$, $K^+$, $HCO_3^-$, $Cl^-$ | ? |
| 4. | $Cit^{3-}$, $Ca^{2+}$, $Na^+$, $Mg^{2+}$, $K^+$, $HCO_3^-$, $Cl^-$ | $Cit^{3-}$, $Ca^{2+}$, $Na^+$, $Mg^{2+}$, $K^+$, $HCO_3^-$, $Cl^-$ | ? |

Reasonable flow rates of blood (125 mL/min) and dialysis fluid (2500 mL/h) (varied within reason), normal steady state concentrations of calcium (2.5 mM) and magnesium (0.9 mM), and suitable concentrations of ions in the anticoagulation fluid and dialysis fluid (varied) are assumed as well as a hematocrit (Hct) of 30%, an albumin plasma concentration of 40 g/L, and a pCO2 of 40 mmHg. A disposable set with a dialyzer with a KoA for urea of 420 is assumed. This is sufficient for clearance to be determined only by the fluid flow rates.

Calculations were done using the following standard fluids (only or as a base); dialysis fluid PrismaSate® B22GK4/0 (PS) (0.75 mM Mg2+, 140 mM Na+, 4 mM K+, 120.5 mM Cl-, 3 mM lactate, 22 mM HCO3-, 110 mM glucose); anticoagulation fluid Prismocitrate® 10/2 (PC) (12 mM citrate (10 mM from Na3cit and 2 mM form H3cit), 136 mM Na+, 106 mM Cl-); and anticoagulation fluid ACD-A (113 mM citrate (75 mM from Na3cit and 38 mM form H3cit), 225 mM Na+, 136 mM D-glucose). The calcium infusion fluid for the calcium syringe contained 225 mM calcium gluconate.

Results
Modality 1
Examples are shown in Table 3.

TABLE 3

Modality 1. Examples when using the dialysis fluid PrismaSate® B22GK4/0 (PS) and combining it with the anticoagulation fluid Prismocitrate® 10/2 (PC) or the anticoagulation fluid ACD-A.

| | Into dialyzer | | | After dialyzer | | | | |
|---|---|---|---|---|---|---|---|---|
| Fluids | Total $Ca^{2+}$ | Ionized $Ca^{2+}$ | Total citrate | Total $Ca^{2+}$ | Ionized $Ca^{2+}$ | Infused $Ca^{2+}$ | Clearance | Total citrate |
| PS PC | 1.9 | 0.40 | 3.1 | 1.3 | 0.36 | 6.2 mM/h | 2955 mL/h | 2.0 |
| PS ACD-A | 2.4 | 0.40 | 4.3 | 1.4 | 0.36 | 5.7 mM/h | 2536 mL/h | 2.3 |

Since the anticoagulation fluid ACD-A fluid is much more concentrated than the dialysis fluid PrismaSate®, the blood flow is less diluted, and therefore the total calcium concentration into the dialyzer is higher. As a consequence the total citrate into the patient is a bit higher in this case and the need for infused calcium is slightly lower. The bicarbonate concentration into the patient is a bit higher. Since the flow rate into the dialyzer is lower, the clearance of the treatment becomes lower.

Modality 2

In this case, calcium is added to the standard dialysis fluid. The blood flow rate is set to 125 ml/min and the citrate and calcium concentrations and the flow rate of the dialysis fluid may be varied. In order to have any chance of receiving correct (<0.4 mM) ionized calcium as well as correct total calcium (2.5 mM) without infusion of calcium fluid, the ionized calcium concentration into the dialyzer was set to different values between 0.25 and 0.4 mM. It is not possible to obtain high enough plasma total calcium concentration out of the dialyzer (into the patient) with a ionized calcium concentration <0.4 mM, no matter how the dialysis fluid flow rate and the calcium concentration in the dialysis fluid are changed. Examples are shown in Table 4. In the case with the anticoagulation fluid ACD-A, the bicarbonate concentration was too high, i.e. the bicarbonate concentration must be lower than 22 mM in the dialysis fluid (which is the concentration in the dialysis fluid PrismaSate® B22GK4/0).

TABLE 4

Modality 2. Examples when using the dialysis fluid PrismaSate® B22GK4/0 (PS) and adding Ca2+ to the dialysis fluid, and combining it with the anticoagulation fluid Prismocitrate® 10/2 (PC) or the anticoagulation fluid ACD-A.

| | Into dialyzer | | | After dialyzer | | | | |
|---|---|---|---|---|---|---|---|---|
| Fluids | Total $Ca^{2+}$ | Ionized $Ca^{2+}$ | Total citrate | Total $Ca^{2+}$ | Ionized $Ca^{2+}$ | Infused $Ca^{2+}$ | Clearance | Total citrate |
| PS + $Ca^{2+}$, PC | 1.7 | 0.25 | 4.0 | (2.1) | 0.4 | — | (2544) | (3.4) not sufficient effect |
| PS + $Ca^{2+}$ ACD-A | 2.4 | 0.25 | 6.0 | (2.0) | 0.4 | — | (2556) | (3.3) not sufficient effect |

This modality does not seem to work neither theoretically, nor clinically. In clinical tests, it has not been possible to perform this kind of dialysis without need for infusion of calcium or clotting of the patients' blood (Gupta 20045, Cointault 20046).

Modality 3

In this case, calcium and citrate are added to the modified standard dialysis fluid. The concentrations of the included electrolytes were changed until correct values out of the dialyzer were achieved (alternatively, the dialysis fluid flow rate was changed). When using the anticoagulation fluid Prismocitrate® 10/12 (PC), the concentrations in the dialysis fluid may be: 3.35 mM Ca2+, 7.0 mM citrate, 1.2 mM Mg2+, 142 mM Na+, 5.9 mM K+, 107 mM Cl−, 29 mM bicarbonate, and the dialysis fluid flow 2500 mL/h (see results in Table 5). When using the anticoagulation fluid ACD-A, the concentrations in the dialysis fluid may be: 2.4 mM Ca2+, 4.8 mM citrate, 0.9 mM Mg2+, 136 mM Na+, 4.2 mM K+, 112 mM Cl−, 20 mM bicarbonate, and the dialysis fluid flow 2500 mL/h (see results in Table 5).

since it has become diluted by the anticoagulation fluid. Different citrate concentrations in the anticoagulation fluids were investigated, and the concentration of Cl− in this fluid depends on the chosen citrate concentration. The concentration of citrate in the dialysis fluid was chosen in order to keep the ionized calcium concentration constant through the dialyzer.

Three different anticoagulation fluids were investigated, one based on the anticoagulation fluid Prismocitrate® 10/12, one on the anticoagulation fluid ACD-A, and one anticoagulation fluid with a citrate concentration in between.

Examples are shown in Table 6.

Alternative 1: To the anticoagulation fluid Prismocitrate® 10/12 was added 2.5 mM Ca2+, 0.9 mM Mg2+ and 4.0 mM K+. In combination therewith, the dialysis fluid contained 2.1 mM Ca2+, 4.1 mM citrate, 0.8 mM Mg2+, 144 mM Na+, 4.0 mM K+, 122 mM Cl−, 20 mM bicarbonate with a dialysis fluid flow of 2500 mL/h.

Alternative 2: Citrate in a fluid may come from Na3cit or H3cit or a combination. In order to receive as high pH as

TABLE 5

Modality 3. Examples when using the dialysis fluid PrismaSate ® B22GK4/0 (PS) and adding Ca2+ and citrate to the dialysis fluid and combining it with the anticoagulation fluid Prismocitrate ® 10/2 (PC) or the anticoagulation fluid ACD-A.

| | Into dialyzer | | | After dialyzer | | | | |
|---|---|---|---|---|---|---|---|---|
| Fluids | Total $Ca^{2+}$ | Ionized $Ca^{2+}$ | Total citrate | Total $Ca^{2+}$ | Ionized $Ca^{2+}$ | Infused $Ca^{2+}$ | Clearance | Total citrate |
| PS + $Ca^{2+}$ and cit PC | 1.9 | 0.40 | 3.1 | 2.5 | 0.40 | — | 2962 | 4.5 |
| PS + $Ca^{2+}$ and cit ACD-A | 2.4 | 0.40 | 4.3 | 2.5 | 0.40 | — | 2538 | 4.5 |

For the anticoagulation fluid Prismocitrate® 10/12, if the dialysis fluid flow rate is changed to 2000 (or 3000) mL/h, then the concentrations out of the dialyzer are slightly affected (compared with concentrations in table 5 above); e.g. total Ca2+ 2.4 (2.6) mM, total Mg2+ 0.8 (0.9) mM and total K+ 3.6 (4.4), and the clearances become 2666 (3253) mL/h. When changing the dialysis fluid flow rate in the example with the anticoagulation fluid ACD-A, the concentrations are affected as well but to a smaller extent.

Modality 4

In this case, the goal was to keep the concentrations of the included electrolytes constant through the dialyzer. When possible, both anticoagulation fluid and dialysis fluid contained normal total plasma values of Ca2+, Na+, K+, Mg2+ and Cl−. However, the Ca2+ and Mg2+ concentrations in the dialysis fluid were slightly lower than normal due to that the plasma flow through the dialyzer needs to be concentrated possible (about 6.4), i.e. as close to the normal plasma pH of 7.4 as possible, all citrate should come from Na3cit. The desired Na+ concentration in the anticoagulation fluid is 140 mM and the citrate concentration in this case would be 140/3=67.6 mM. 2.5 mM Ca2+, 0.9 mM Mg2+ and 4.0 mM K+ was added to this anticoagulation fluid. In combination therewith, the dialysis fluid contained 2.25 mM Ca2+, 4.5 mM citrate, 0.85 mM Mg2+, 140 mM Na+, 4.0 mM K+, 122 mM Cl−, 15 mM bicarbonate with a dialysis fluid flow of 2500 mL/h.

Alternative 3: To the anticoagulation fluid ACD-A was added 2.5 mM Ca2+, 0.9 mM Mg2+ and 4.0 mM K+. In combination therewith, the dialysis fluid contained 2.25 mM Ca2+, 4.5 mM citrate, 0.85 mM Mg2+, 140 mM Na+, 4.0 mM K+, 122 mM Cl−, 15 mM bicarbonate with a dialysis fluid flow of 2500 mL/h.

TABLE 6

Modality 4. Examples when using the dialysis fluid PrismaSate ® B22GK4/0 (PS) and adding Ca2+ and citrate to the dialysis fluid and combining it with three different anticoagulation fluids based on the anticoagulation fluid Prismocitrate ® 10/12, the anticoagulation fluid ACD-A or one anticoagulation fluid with a citrate concentration in between.

| Fluids | Into dialyzer | | | After dialyzer | | | | |
|---|---|---|---|---|---|---|---|---|
| | Total $Ca^{2+}$ | Ionized $Ca^{2+}$ | Total citrate | Total $Ca^{2+}$ | Ionized $Ca^{2+}$ | Infused $Ca^{2+}$ | Clearance | Total citrate |
| PS + $Ca^{2+}$ and cit PC 10/2 + $Ca^{2+}$ | 2.5 | 0.40 | 4.8 | 2.5 | 0.40 | — | 3409 | 4.6 |
| PS + $Ca^{2+}$ and cit 67.6 citrate + $Ca^{2+}$ | 2.5 | 0.40 | 4.6 | 2.5 | 0.40 | — | 2622 | 4.5 |
| PS + Ca2+ and cit ACD-A + $Ca^{2+}$ | 2.5 | 0.40 | 4.5 | 2.5 | 0.40 | — | 2539 | 4.5 |

The flow rates of dialysis fluid (1000-4500 mL/h, with a constant blood flow rate of 125 mL/min) and blood (50-200 mL/min, with a constant dialysis fluid rate of 2500 mL/h) may be widely varied without any significant influence on the electrolyte concentrations, except bicarbonate.

Evaluation

Modality 1 is the treatment technique used today when performing citrate dialysis. It would be desirable to avoid the calcium infusion that is necessary for this treatment. This cannot be achieved with modality 2 but with 3 and 4. Modality 3 and 4 are comparable regarding the total citrate concentration the patient is subjected to, but modality 4 is much more insensitive to changes in the flow rates of blood, dialysis fluid and anticoagulation fluid since the system is closer to equilibrium through the dialyzer in modality 4.

Detailed Description of the Drawings

In FIG. 1 is shown a system for regional citrate anticoagulation in an extracorporeal blood circuit comprising an arterial blood line 1 configured to be connected to a vascular access (not shown) for withdrawing blood from a patient and a venous blood line 2 configured to be connected to the vascular access (not shown) for returning blood to the patient. This system comprises a filter 3 with a dialysate side and a blood side, which blood side is in fluid communication with the arterial blood line 1 and venous blood line 2; a pre-filter infusion line 4 connected to the arterial blood line 2 upstream the filter 3 for infusing an anticoagulation fluid 5 containing citrate into blood in the arterial blood line 1; and a post-filter infusion line 6 connected to the venous blood line 2 downstream the filter 3 for infusing an infusion fluid 7 comprising 2-8 mM citrate and 1-5 mM total calcium into blood in the venous blood line 2. An effluent bag 8 is provided in fluid communication with the dialysate side of the filter 3, to collect the plasma water (ultrafiltrate) withdrawn from the blood passing the filter 3.

Figure 2:
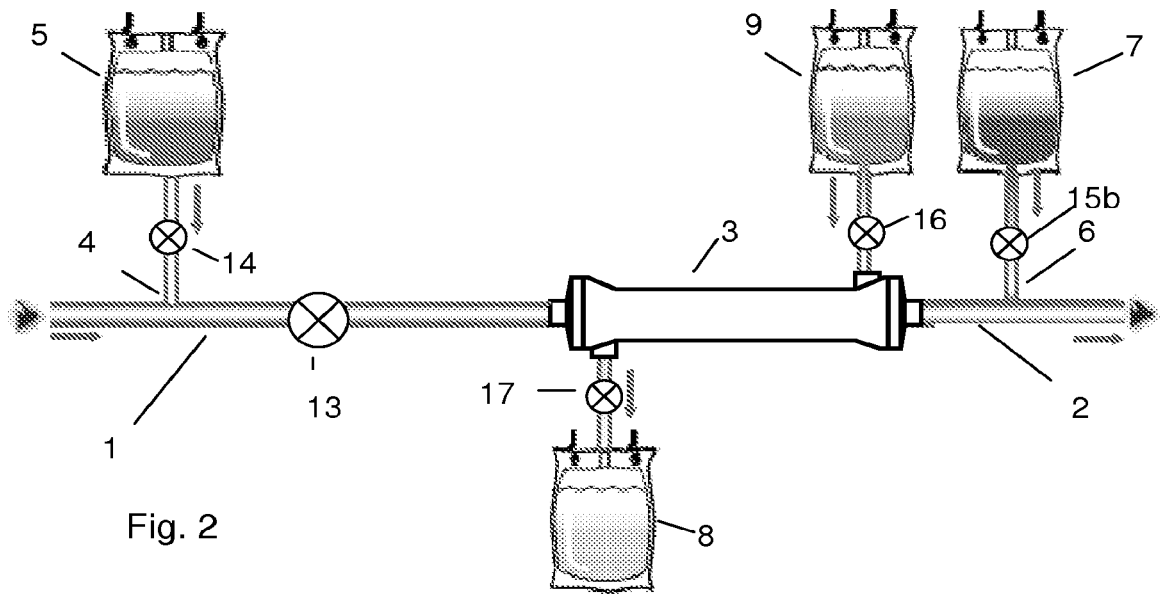

In FIG. 2 is shown another embodiment of the system in FIG. 1 with the addition that the dialysate side of the filter 3 is in fluid communication with a dialysis fluid 9 comprising 2-8 mM citrate and 1-5 mM total calcium.

Figure 3:
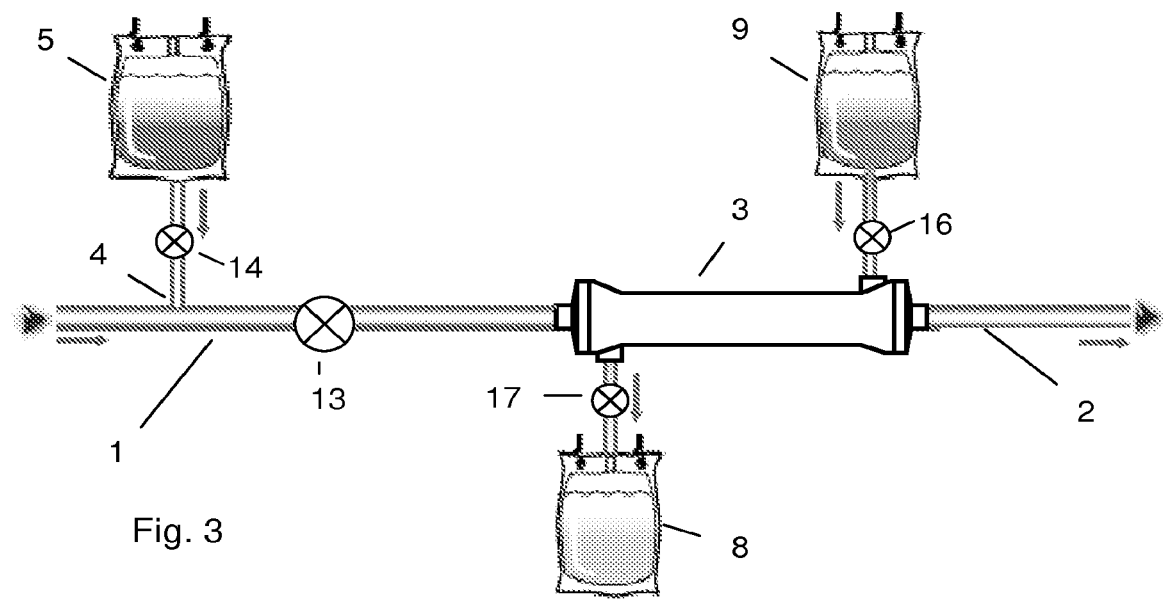

In FIG. 3 is shown another system for regional citrate anticoagulation in an extracorporeal blood circuit. This system includes an arterial blood line 1 configured to be connected to a vascular access for withdrawing blood from a patient and a venous blood line 2 configured to be connected to the vascular access for returning blood to the patient. This system also comprises a filter 3 with a dialysate side and a blood side, which blood side is in fluid communication with the arterial and venous blood lines, and which dialysate side is in fluid communication with a dialysis fluid 9 comprising 2-8 mM citrate and 1-5 mM total calcium and an effluent bag 8 for the spent dialysis fluid and the plasma water (ultrafiltrate) withdrawn from the blood passing the filter 3. The system further comprises a pre-filter infusion line 4 connected to the arterial blood line 1 upstream the filter 3 for infusing an anticoagulation fluid 5 containing citrate into the blood in the arterial blood line.

Figure 4:
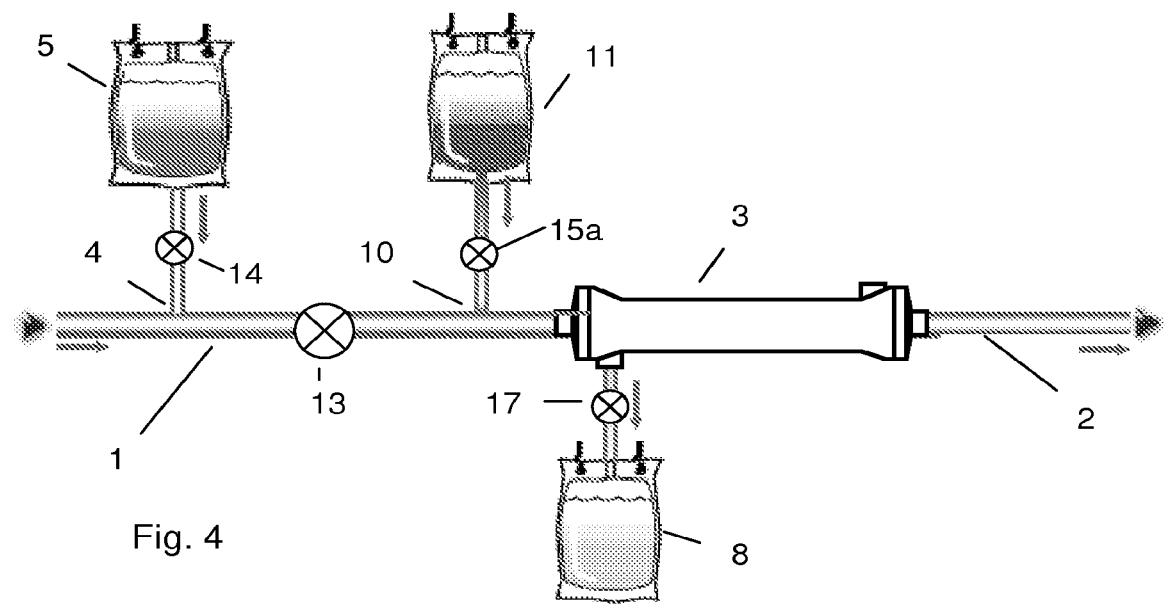

In FIG. 4 is shown yet another embodiment of the system for regional citrate anticoagulation in an extracorporeal blood circuit according to the present invention. This system includes an arterial blood line 1 configured to be connected to a vascular access for withdrawing blood from a patient and a venous blood line 2 configured to be connected to the vascular access for returning blood to the patient. This system further comprises a filter 3 with a dialysate side and a blood side, which blood side is configured in fluid communication with the arterial and venous blood lines. A pre-filter infusion line 4 is connected to the arterial blood line 1 upstream the filter 3 for infusing an anticoagulation fluid 5 containing citrate into blood in the arterial blood line 1. A second pre-filter infusion line 10 is connected to the arterial blood line 1 upstream the filter 3 for infusing an infusion fluid 11 comprising 2-8 mM citrate and 1-5 mM total calcium into blood in the arterial blood line 1. Also here an effluent bag 8 is provided in fluid communication with the dialysate side of the filter 3, for receiving the plasma water (ultrafiltrate) withdrawn from the blood passing the filter 3.

Figure 5:
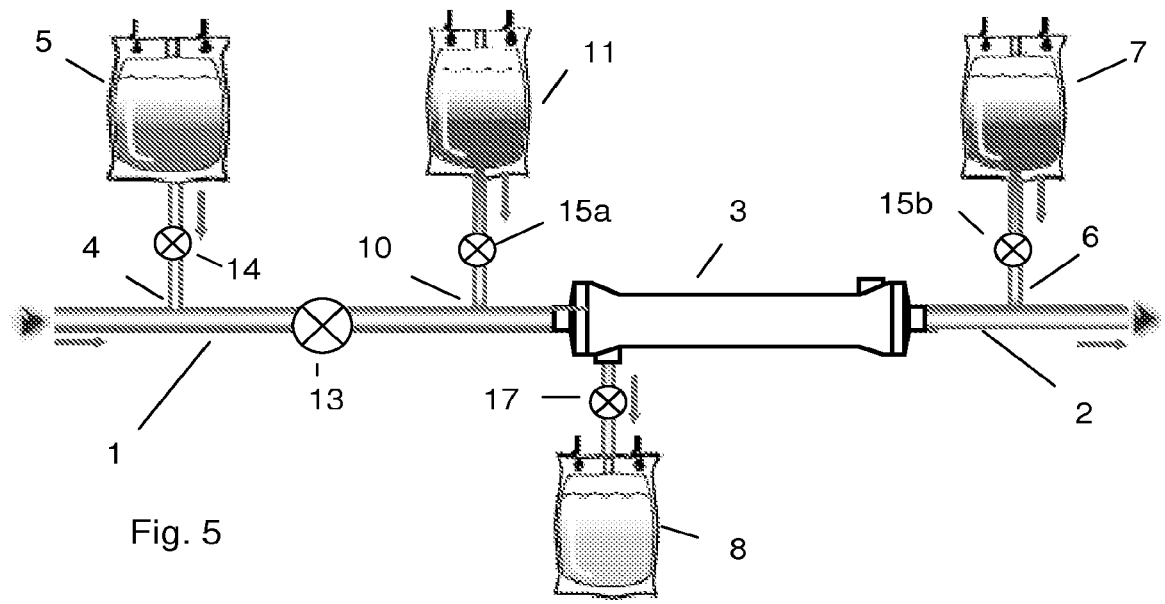

In FIG. 5 is another embodiment of the system in FIG. 4 shown, which further comprises a post-filter infusion line 6 connected to the venous blood line 2 downstream the filter 3 for infusing an infusion fluid 7 comprising 2-8 mM citrate and 1-5 mM total calcium into blood in the venous blood line 2.

Figure 6:
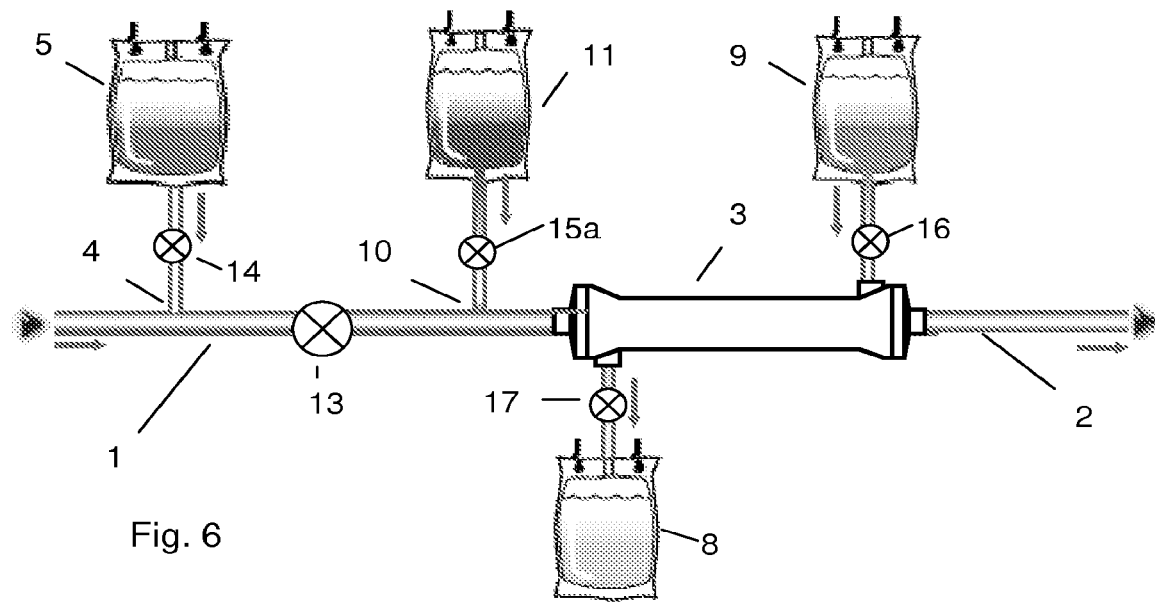

In FIG. 6 is yet another embodiment of the system in FIG. 4 shown, wherein the dialysate side of the filter 3 is in fluid communication with a dialysis fluid 9 comprising 2-8 mM citrate and 1-5 mM total calcium.

Figure 7:
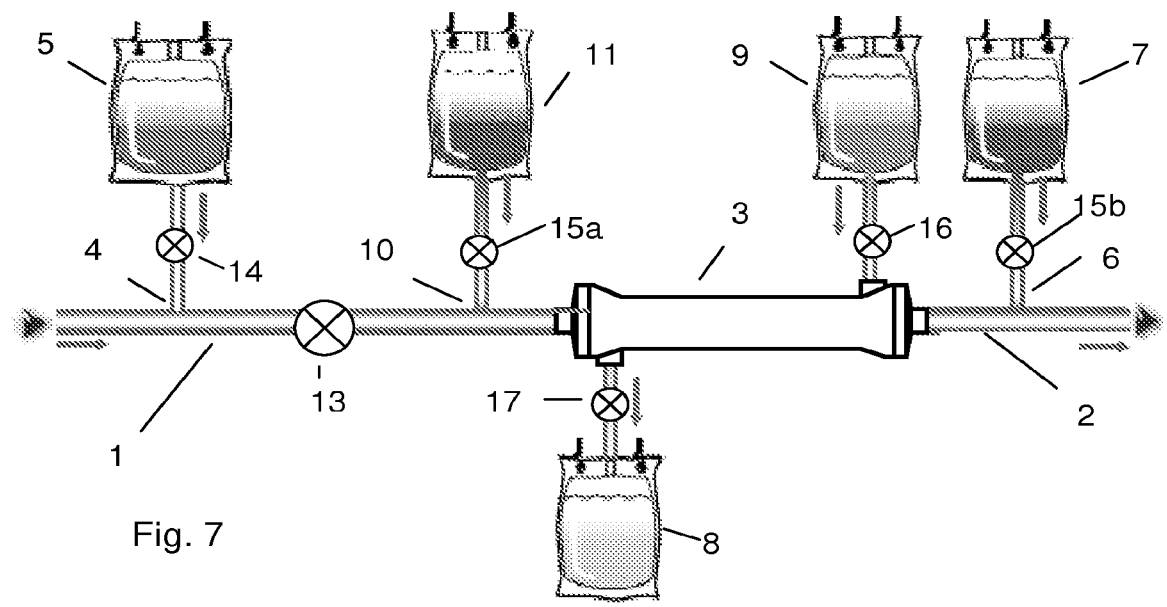

In FIG. 7 is another embodiment of the system in FIG. 6 shown. This system further comprises a post-filter infusion line 6 connected to the venous blood line 2 downstream the filter 3 for infusing an infusion fluid 7 comprising 2-8 mM citrate and 1-5 mM total calcium into the blood in the venous blood line 2.

Figure 8:
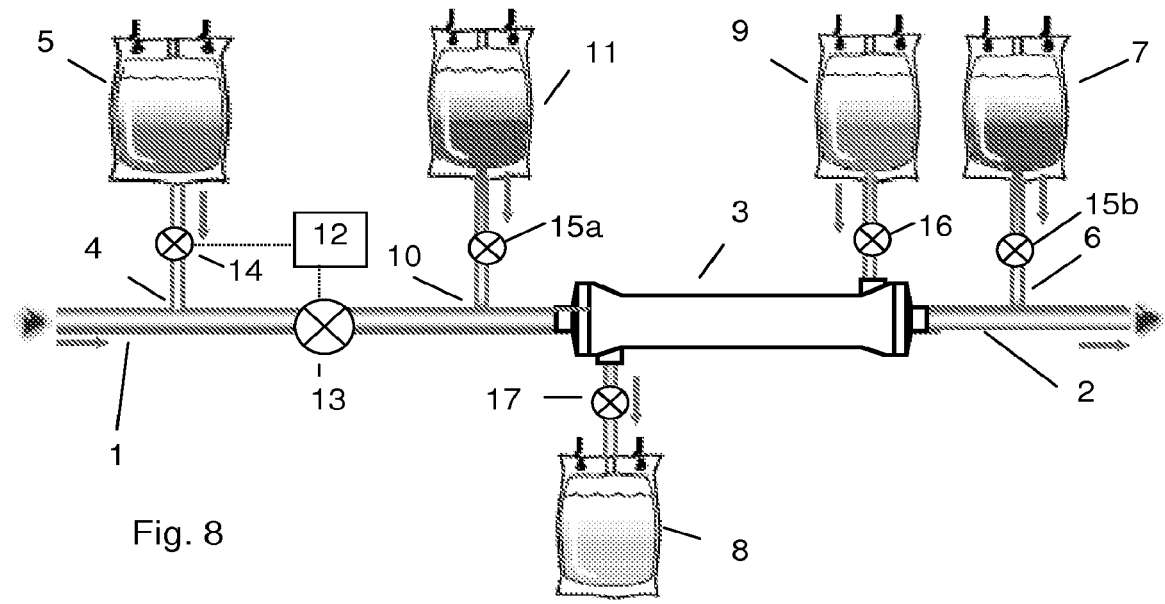

In FIG. 8 is another embodiment of the systems above shown, which further comprises a control unit 12 adapted to control the anticoagulation fluid flow rate in relation to the blood flow rate. Such a control unit may be provided in all the systems shown in the different embodiments of FIG. 1-FIG. 7. By having such a control unit 12, the system is monitoring and securing that the amount of citrate within the blood is enough to maintain anticoagulation within the extracorporeal blood circuit.

As is evident from all the figures above, the systems do not comprise any post-filter infusion line connected to the venous blood line 2 downstream the filter 3 for infusion of a fluid comprising >6 mM total calcium.

In the systems according to the invention, pumps are configured to pump blood (pump 13) through the extracorporeal blood circuit, anticoagulation fluid (pump 14) into the extracorporeal blood circuit, infusion fluid (pumps 15a and 15b) into the extracorporeal blood circuit, dialysis fluid (pump 16) into the dialysate side of the filter 3, and plasma liquid (ultrafiltrate) and optional spent dialysis fluid (pump 17) out from the dialysate side of the filter 3 and into the effluent bag 8.

It should be understood that various changes and modifications to the presently preferred embodiments described herein will be apparent to those skilled in the art. Such changes and modifications may be made without departing from the spirit and scope of the present invention and without diminishing its attendant advantages. It is therefore intended that such changes and modifications be covered by the appended claims.

The invention is claimed as follows:

1. A system for regional citrate anticoagulation in an extracorporeal blood circuit comprising:
   an arterial blood line for withdrawing blood from a patient;
   a venous blood line for returning blood to the patient;
   a pump configured to be coupled to the arterial blood line or the venous blood line and to pump blood simultaneously through both the arterial blood line and the venous blood line;
   a filter including a dialysate side and a blood side, wherein the blood side is in fluid communication with the arterial and venous blood lines;
   a first pre-filter infusion line in fluid communication with the arterial blood line upstream of the filter and an anticoagulation fluid source containing at least 8 mM citrate to be infused into the blood stream via the arterial blood line; and
   a second pre-filter infusion line in fluid communication with the arterial blood line upstream of the filter and an infusion fluid source comprising 2-8 mM citrate and 1-5 mM total calcium to be infused into the blood stream via the arterial blood line.

2. The system for regional citrate anticoagulation in an extracorporeal blood circuit according to claim 1, the infusion fluid source a first infusion fluid source, and which further includes a post-filter infusion line in fluid communication with the venous blood line downstream of the filter and a second infusion fluid source including 2-8 mM citrate and 1-5 mM total calcium to be infused into the blood stream via the venous blood line.

3. The system for regional citrate anticoagulation in an extracorporeal blood circuit according to claim 2, further comprising a pump configured to be coupled to the second pre-filter infusion line to pump the first infusion fluid source into the blood stream via the arterial blood line; and a pump configured to be coupled to the post-filter infusion line to pump the second infusion fluid source into the blood stream via the venous blood line.

4. The system for regional citrate anticoagulation in an extracorporeal blood circuit according to claim 1, wherein the dialysate side of the filter is in fluid communication with a dialysis fluid source comprising 2-8 mM citrate and 1-5 mM total calcium.

5. The system for regional citrate anticoagulation in an extracorporeal blood circuit according to claim 1, wherein the anticoagulation fluid further comprises 1.5-4 mM total calcium.

6. The system for regional citrate anticoagulation in an extracorporeal blood circuit according to claim 5, wherein the anticoagulation fluid comprises 2-3 mM total calcium.

7. The system for regional citrate anticoagulation in an extracorporeal blood circuit according to claim 5, wherein the anticoagulation fluid comprises 2.2-2.6 mM total calcium.

8. The system for regional citrate anticoagulation in an extracorporeal blood circuit according to claim 5, wherein the anticoagulation fluid comprises 2.4 mM total calcium.

9. The system for regional citrate anticoagulation in an extracorporeal blood circuit according to claim 1, wherein the anticoagulation fluid further comprises at least one of 0-1.5 mM magnesium, 0-5.0 mM potassium, 0-11 mM glucose, 130-150 mM sodium, or 0-140 mM chloride.

10. The system for regional citrate anticoagulation in an extracorporeal blood circuit according to claim 1, wherein the system further comprises a control unit configured to control the anticoagulation fluid flow rate in relation to a blood flow rate provided by the pump.

11. The system for regional citrate anticoagulation in an extracorporeal blood circuit according to claim 1, wherein the citrate comprises sodium citrate.

12. The system for regional citrate anticoagulation in an extracorporeal blood circuit according to claim 1, wherein the infusion fluid source further comprises a physiological buffer.

13. The system for regional citrate anticoagulation in an extracorporeal blood circuit according to claim 12, wherein the physiological buffer includes bicarbonate.

14. The system for regional citrate anticoagulation in an extracorporeal blood circuit according to claim 13, wherein the bicarbonate is no more than 3.1 mM in the infusion fluid source.

15. The system for regional citrate anticoagulation in an extracorporeal blood circuit according to claim 1, wherein the infusion fluid source further comprises 0.1-3.0 mM gluconic acid.

16. The system for regional citrate anticoagulation in an extracorporeal blood circuit according to claim 1, wherein the infusion fluid source further comprises 3.0-5.0 mM citrate and 1.8-2.4 mM total calcium.

17. The system for regional citrate anticoagulation in an extracorporeal blood circuit according to claim 1, wherein the infusion fluid source further comprises at least one of 0-1.5 mM magnesium, 0-5.0 mM potassium, 0-11 mM glucose, 130-150 mM sodium and 80-150 mM chloride, or 0-2.8 mM phosphate.

18. The system for regional citrate anticoagulation in an extracorporeal blood circuit according to claim 1, wherein the post-filter infusion line is not connected to any infusion fluid sources comprising more than 6 mM total calcium.

19. The system for regional citrate anticoagulation in an extracorporeal blood circuit according to claim 1, wherein the infusion fluid source comprises 2-3 mM total calcium.

\* \* \* \* \*